(12) United States Patent
Waller et al.

(10) Patent No.: US 11,471,506 B2
(45) Date of Patent: Oct. 18, 2022

(54) VIP ANTAGONISTS AND USES IN TREATING CANCER

(71) Applicants: Emory University, Atlanta, GA (US); Georgia Tech Research Corporation, Atlanta, GA (US)

(72) Inventors: Edmund K. Waller, Atlanta, GA (US); Rebecca Pankove, Atlanta, GA (US); Susan Thomas, Atlanta, GA (US); Sruthi Ravindranathan, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 17/050,376

(22) PCT Filed: Apr. 24, 2019

(86) PCT No.: PCT/US2019/028914
§ 371 (c)(1),
(2) Date: Oct. 23, 2020

(87) PCT Pub. No.: WO2019/209952
PCT Pub. Date: Oct. 31, 2019

(65) Prior Publication Data
US 2021/0046152 A1 Feb. 18, 2021

Related U.S. Application Data

(60) Provisional application No. 62/661,236, filed on Apr. 23, 2018.

(51) Int. Cl.
*A61K 38/00* (2006.01)
*A61K 38/16* (2006.01)
*A61P 35/00* (2006.01)
*C07K 16/28* (2006.01)

(52) U.S. Cl.
CPC ............ *A61K 38/16* (2013.01); *A61P 35/00* (2018.01); *C07K 16/2818* (2013.01); *C07K 16/2827* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 5,225,539 A | 7/1993 | Winter |
| 5,565,424 A | 10/1996 | Gozes et al. |
| 5,585,089 A | 12/1996 | Queen et al. |
| 5,693,761 A | 12/1997 | Queen et al. |
| 5,693,762 A | 12/1997 | Queen et al. |
| 5,859,205 A | 1/1999 | Adair et al. |
| 6,300,064 B1 | 10/2001 | Knappik et al. |
| 6,407,213 B1 | 6/2002 | Carter et al. |
| 6,828,304 B1 | 12/2004 | Burman et al. |
| 7,094,755 B2 | 8/2006 | Burman et al. |
| 7,125,689 B2 | 10/2006 | Carr et al. |
| 7,264,806 B2 | 9/2007 | Carr et al. |

OTHER PUBLICATIONS

National Institudes of Health, PDL1 (Immunotherapy) Tests, last visited, Oct. 28, 2021.*
Siedel et al. 2018, Anti-PD-1 and Anti-CTLA-4 Therapies in Cancer: Mechanisms of Action, Efficacy, and Limitations. Frontiers in oncology, 8: 86.*
Yao et al. (2018) Cancer Cell-Intrinsic PD-1 and Implications in Combinatorial Immunotherapy. Front. Immunol. 9:1774.*
Brentjens, Renier J., et al. "CD19-targeted T cells rapidly induce molecular remissions in adults with chemotherapy-refractory acute lymphoblastic leukemia." Science translational medicine 5.177 (2013): 177ra38-177ra38.
Filaci, Gilberto, et al. "CD8+ CD28− T regulatory lymphocytes inhibiting T cell proliferative and cytotoxic functions infiltrate human cancers." The Journal of Immunology 179.7 (2007): 4323-4334.
Hodi, F. Stephen, et al. "Improved survival with ipilimumab in patients with metastatic melanoma." New England Journal of Medicine 363.8 (2010): 711-723.
Montes, Carolina L., et al. "Tumor-induced senescent T cells with suppressor function: a potential form of tumor immune evasion." Cancer research 68.3 (2008): 870-879.
Pentcheva-Hoang, Tsvetelina, Emily Corse, and James P. Allison. "Negative regulators of T-cell activation: potential targets for therapeutic intervention in cancer, autoimmune disease, and persistent infections." Immunological reviews 229.1 (2009): 67-87.
Petersen, Christopher, Jian-Ming Li, and Edmund Waller. "Administration of a vasoactive intestinal peptide antagonist significantly enhances the autologous anti-leukemia T cell response in a murine model of AML." Journal for ImmunoTherapy of Cancer 3.2 (2015): 1-4., 3(Suppl 2):P238.
Porter, David L., et al. "A phase 1 trial of donor lymphocyte infusions expanded and activated ex vivo via CD3/CD28 costimulation." Blood 107.4 (2006): 1325-1331.
Ramello, María Cecilia, et al. "Tumor-induced senescent T cells promote the secretion of pro-inflammatory cytokines and angiogenic factors by human monocytes/macrophages through a mechanism that involves Tim-3 and CD40L." Cell death & disease 5.11 (2014): e1507-e1507.
Schudel et al. "S-Nitrosated Polypropylene Sulfi de Nanoparticles for Thiol-Dependent Transnitrosation and Toxicity Against Adult Female Filarial Worms" Adv. Healthcare Mater. 2015, 4, 1484-1490.

(Continued)

*Primary Examiner* — Jeanette M Lieb
(74) *Attorney, Agent, or Firm* — Meunier Carlin & Curfman LLC

(57) ABSTRACT

This disclosure relates to methods of treating cancer or viral infections comprising administering an effective amount of a VIP antagonist in combination with an immune check-point inhibitor to a subject in need thereof. In certain embodiments, the immune check-point inhibitor is an anti-PD1 or anti-PDL1 antibody.

15 Claims, 6 Drawing Sheets
Specification includes a Sequence Listing.

(56) References Cited

OTHER PUBLICATIONS

Sharma, P., & Allison, J. P. (2015). The future of immune checkpoint therapy. Science, 348(6230), 56-61. doi:10.1126/science.aaa8172.

Thomas, Susan N., et al. "Targeting the tumor-draining lymph node with adjuvanted nanoparticles reshapes the anti-tumor immune response." Biomaterials 35.2 (2014): 814-824.

* cited by examiner

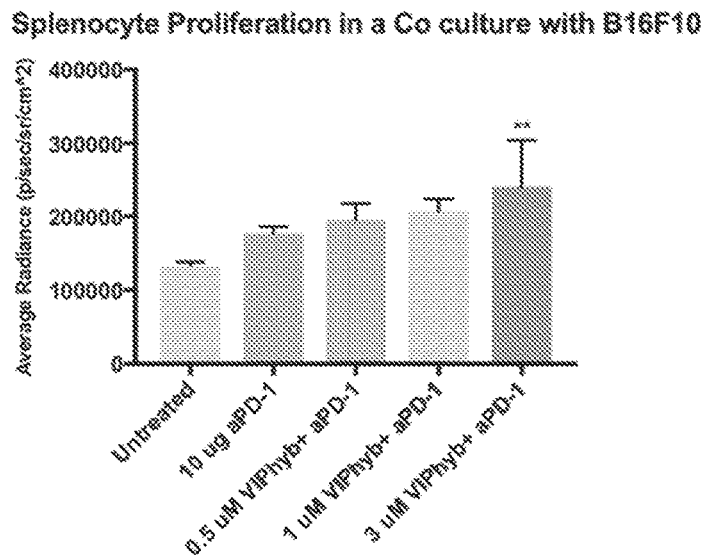
FIG. 2A
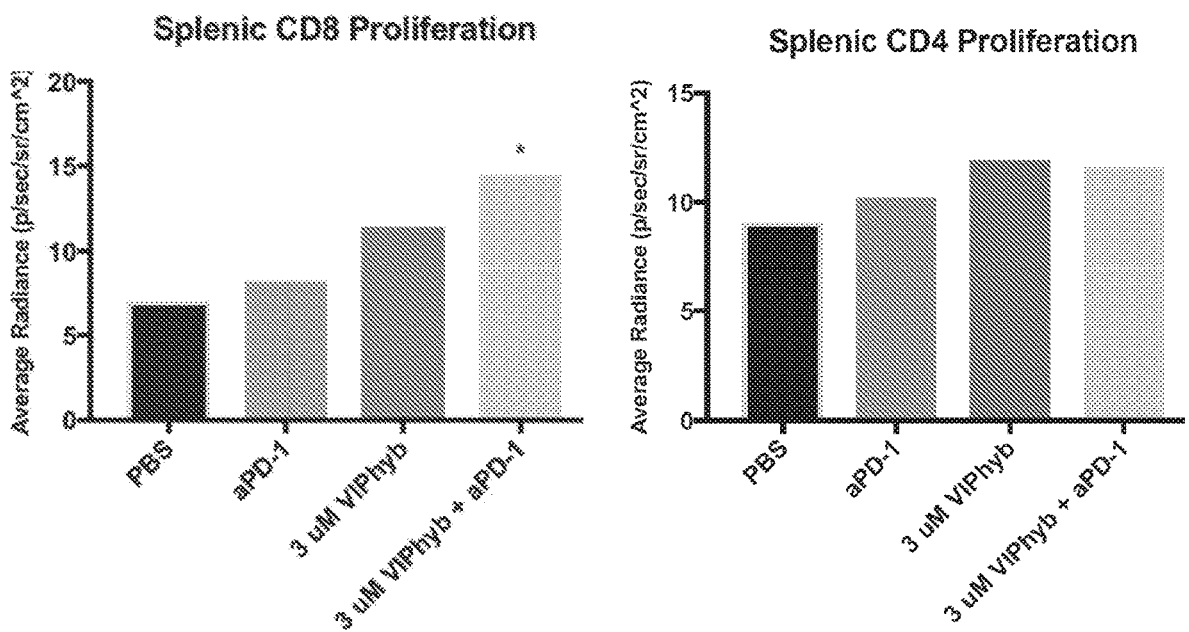
FIG. 2B
FIG. 2C

SEQUENCE LISTING

<160> NUMBER OF SEQ ID NOS: 11

<210> SEQ ID NO 1
<211> LENGTH: 28
<212> TYPE: PRT
<213> ORGANISM: Artificial
<220> FEATURE:
<223> OTHER INFORMATION: Synthetic construct

<400> SEQUENCE: 1

Lys Pro Arg Arg Pro Tyr Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 28
<212> TYPE: PRT
<213> ORGANISM: Artificial
<220> FEATURE:
<223> OTHER INFORMATION: Synthetic construct

<400> SEQUENCE: 2

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 3
<211> LENGTH: 34
<212> TYPE: PRT
<213> ORGANISM: Artificial
<220> FEATURE:
<223> OTHER INFORMATION: Synthetic construct

<400> SEQUENCE: 3

Lys Pro Arg Arg Pro Tyr Thr Asp Asn Tyr Thr Arg Leu Arg Lys Gln
1               5                   10                  15

Met Ala Val Lys Lys Tyr Leu Asn Ser Ile Leu Asn Gly Gly Gly Gly
            20                  25                  30

Ser Cys

<210> SEQ ID NO 4
<211> LENGTH: 29
<212> TYPE: PRT
<213> ORGANISM: Artificial
<220> FEATURE:
<223> OTHER INFORMATION: Synthetic construct

<400> SEQUENCE: 4

Tyr Phe Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 5
<211> LENGTH: 23
<212> TYPE: PRT
<213> ORGANISM: Artificial
<220> FEATURE:
<223> OTHER INFORMATION: Synthetic construct

<400> SEQUENCE: 5

Phe Thr Asp Asn Tyr Thr Arg Leu Arg Lys Gln Met Ala Val Lys Lys

```
                1               5                   10                  15
Tyr Leu Asn Ser Ile Leu Asn
            20

<210> SEQ ID NO 6
<211> LENGTH: 28
<212> TYPE: PRT
<213> ORGANISM: Artificial
<220> FEATURE:
<223> OTHER INFORMATION: Synthetic construct

<400> SEQUENCE: 6

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
            20                  25

<210> SEQ ID NO 7
<211> LENGTH: 6
<212> TYPE: PRT
<213> ORGANISM: Artificial
<220> FEATURE:
<223> OTHER INFORMATION: Synthetic construct

<400> SEQUENCE: 7

Lys Pro Arg Arg Pro Tyr
1               5

<210> SEQ ID NO 8
<211> LENGTH: 22
<212> TYPE: PRT
<213> ORGANISM: Artificial
<220> FEATURE:
<223> OTHER INFORMATION: Synthetic construct

<400> SEQUENCE: 8

Thr Asp Asn Tyr Thr Arg Leu Arg Lys Gln Met Ala Val Lys Lys Tyr
1               5                   10                  15

Leu Asn Ser Ile Leu Asn
            20

<210> SEQ ID NO 9
<211> LENGTH: 28
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (17)..(17)
<223> OTHER INFORMATION: Xaa can be any naturally occurring amino acid

<400> SEQUENCE: 9

Lys Pro Arg Arg Pro Tyr Thr Asp Asn Tyr Thr Arg Leu Arg Lys Gln
1               5                   10                  15

Xaa Ala Val Lys Lys Tyr Leu Asn Ser Ile Leu Asn
            20                  25

<210> SEQ ID NO 10
<211> LENGTH: 27
<212> TYPE: PRT
<213> ORGANISM: Artificial
<220> FEATURE:
<223> OTHER INFORMATION: Synthetic construct

<400> SEQUENCE: 10
```

```
His Phe Asp Ala Val Phe Thr Asn Ser Tyr Arg Lys Val Leu Lys Arg
1               5                   10                  15

Leu Ser Ala Arg Lys Leu Leu Gln Asp Ile Leu
                20              25

<210> SEQ ID NO 11
<211> LENGTH: 32
<212> TYPE: PRT
<213> ORGANISM: Artificial
<220> FEATURE:
<223> OTHER INFORMATION: Synthetic construct

<400> SEQUENCE: 11

Thr Asp Ser Tyr Ser Arg Tyr Arg Lys Gln Met Ala Val Lys Lys Tyr
1               5                   10                  15

Leu Ala Ala Val Leu Gly Lys Arg Tyr Lys Gln Arg Val Lys Asn Lys
                20                  25                  30
```

VIP ANTAGONISTS AND USES IN TREATING CANCER

CROSS-REFERENCE TO RELATED APPLICATIONS

This application is the National Stage of International Application No. PCT/US2019/028914 filed Apr. 24, 2019, which claims the benefit of U.S. Provisional Application No. 62/661,236 filed Apr. 23, 2018. The entirety of each of these applications is hereby incorporated by reference for all purposes.

STATEMENT REGARDING FEDERALLY SPONSORED RESEARCH OR DEVELOPMENT

This invention was made with government support under CA207619 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 18102PCT_ST25.txt. The text file is 5 KB, was created on Apr. 24, 2019, and is being submitted electronically via EFS-Web.

BACKGROUND

Melanoma is considered one of the most chemotherapy-resistant malignancies, and efficacy of existing therapies remains poor, with a five-year survival rate of 20% for patients with distant metastases. Therefore, there is a need to identify improved methods of treating melanoma. Hodi et al. report improved survival with ipilimumab in patients with metastatic melanoma. N. Engl. J. Med., (2010), 363, 711-723. Pentcheva-Hoang et al. report negative regulators of T cell activation as potential targets for therapeutic intervention in cancer, autoimmune disease, and persistent infections. Immunol Rev, 2009, 229:67-87. See also Sharma, et al., Science, 2015, 348, 56-61.

Petersen et al. report administration of a vasoactive intestinal peptide antagonist enhances the autologous anti-leukemia T cell response in a murine model of AML. Journal for ImmunoTherapy of Cancer 2015, 3(Suppl 2):P238.

Thomas et al. report targeting the tumor-draining lymph node with adjuvanted nanoparticles reshapes the anti-tumor immune response. Biomaterials 2014, 35 (2): 814-824. Schudel et al. report S-nitrosated polypropylene sulfide nanoparticles. Adv. Healthcare Mater. 2015, 4, 1484-1490.

References cited herein are not an admission of prior art.

SUMMARY

This disclosure relates to VIP antagonists for use in methods of treating cancer. In certain embodiments, this disclosure relates to methods of treating cancer or viral infections comprising administering an effective amount of a VIP antagonist in combination with an immune check-point inhibitor to a subject in need thereof. In certain embodiments, the immune check-point inhibitor is an anti-PD1 or anti-PDL1 antibody.

In certain embodiments, the subject is diagnosed with a cancer selected from the group of melanoma, lung cancer, renal cancer, leukemia, non-Hodgkin's lymphoma, Hodgkin's lymphoma, myeloma, bladder cancer, pancreatic cancer, gastric cancer, esophageal cancer, glioblastoma, colon cancer, breast cancer and prostate cancer.

In certain embodiments, the antibody to an immune check-point molecule is selected from the group of anti-PD1 antibodies including pembrolizumab (Keytruda™) and nivolumab (Opdivo™). In certain embodiments, the antibody to immune check-point molecule is selected from the group of anti-PDL1 antibodies including atezolizumab (Tecentriq™), avelumab (Bavencio™), durvalumab (Imfinzi™). In certain embodiments, the antibody to immune check-point molecule is ipilimumab (Yervoy™).

In certain embodiments, the antagonist of vasoactive intestinal peptide signalling is composed of the sequence N-Term KPRRPYTDNYTRLRKQMAVKKYLNSILN (SEQ ID NO: 1) C-Term. In certain embodiments, the sequence of antagonist of vasoactive intestinal peptide signalling is modified to include a C-terminal link or composed of four glycines, a serine, and a terminal cysteine in order to facilitate coupling to the nanoparticle: N-Term KPRRPYTDNYTRLRKQMAVKKYLNSILNGGGGSC (SEQ ID NO: 3) C-Term. In certain embodiments, the VIP antagonist is selected from the group consisting of [Ac-Tyr1,D-Phe2] GRF 1-29, amide, i.e., (SEQ ID NO: 4) YFDAIFTNSYRKVLGQLSARKLLQDIMSR (Modifications: Tyr-1=N-terminal Ac, Phe-2=D-Phe, Arg-29=C-terminal amide); VIP (6-28), i.e., (SEQ ID NO:5) FTDNYTRLRKQMAVKKYLNSILN (Modifications: Asn-23=C-terminal amide); [D-p-Cl-Phe6, Leu17]-VIP, i.e., (SEQ ID NO:6) HSDAVFTDNYTRLRKQLAVKKYLNSILN (Modifications: Phe-6=p-Cl-D-Phe, Asn=C-terminal amide); VIP-hyb also known as VIPhybrid (SEQ ID NO: 1) KPRRPYTDNYTRLRKQMAVKKYLNSILN, i.e., a hybrid peptide of neurotensin and VIP consisting of an N-terminal (SEQ ID NO:7) KPRRPY, also designated neurotensin (6-11)] followed by the C-terminal 22 amino acids of VIP, i.e., (SEQ ID NO:8) TDNYTRLRKQMAVKKYLNSILN, also designated VIP (7-28); N-terminal Stearyl, Norleucine 17 VIPhyb, i.e., (SEQ ID NO: 9) KPRRPYTDNYTRLRKQXAVKKYLNSILN, wherein X is norleucine; Ac His1 [D-Phe(2), Lys(15), Arg(16), Leu(27)]-VIP (1-7)/GRF(8-27), i.e., (SEQ ID NO:10) HFDAVFTNSYRKVLKRLSARKLLQDIL, C-terminal amide; and pituitary adenylate cyclase-activating polypeptide, PACAP (6-38) C-terminal amide, i.e., (SEQ ID NO:11) TD SYSRYRKQMAVKKYLAAVLGKRYKQRVKNK.

In certain embodiments, the human T cells are activated with anti-CD3 antibody bound to a plate. In certain embodiments, the human T cells are activated in a mixed lymphocyte reaction. In certain embodiments, the human T cells are activated in vitro by co-incubation with tumor-associated antigens. In certain embodiments, the tumor associate antigens are presented on tumor microvesicles. In certain embodiments, the activated human T cells are infused into a human patient with cancer.

In certain embodiments, the human T cells are activated in vitro by co-incubation with viral antigens. In certain embodiments, the viral antigens are presented on microvesicles. In certain embodiments, the viral antigens are presented on dendritic cells. In certain embodiments, the activated human T cells are infused into a human patient with cancer.

In certain embodiments, the human patient with cancer has leukemia. In certain embodiments, the human patient with cancer has lymphoma. In certain embodiments, the human patient with cancer has multiple myeloma. In certain embodiments, the human patient with cancer has an epithelial cancer. In certain embodiments, the human patient has lung cancer. In certain embodiments, the human patient has breast cancer. In certain embodiments, the human patient has colon cancer. In certain embodiments, the human patient has prostate cancer. In certain embodiments, the human patient has malignant melanoma. In certain embodiments, the human patient has brain cancer.

In certain embodiments, this disclosure relates to methods of augmenting anti-cancer immune responses by infusion of a nanoparticle expressing an antagonist of VIP signalling. In certain embodiments, the particle contains the peptide sequence of VIPhyb, KPRRPYTDNYTRLRKQMAVK-KYLNSILN (SEQ ID NO: 1).

BRIEF DESCRIPTION OF THE DRAWINGS

FIG. 2A shows data on splenocytes proliferation in a Co-culture with B16F10 cells, optionally with VIPhyb and an anti-PD-1 antibody. Splenocytes isolated from 3 naïve luciferase+ B6 mouse were cultured with irradiated B16 cells and with or without VIPhyb in triplicate, and proliferation measured with BLI.

FIG. 2B shows data on splenic CD8 proliferation.

FIG. 2C shows data on splenic CD4 proliferation.

DETAILED DESCRIPTION

Figure 1A:
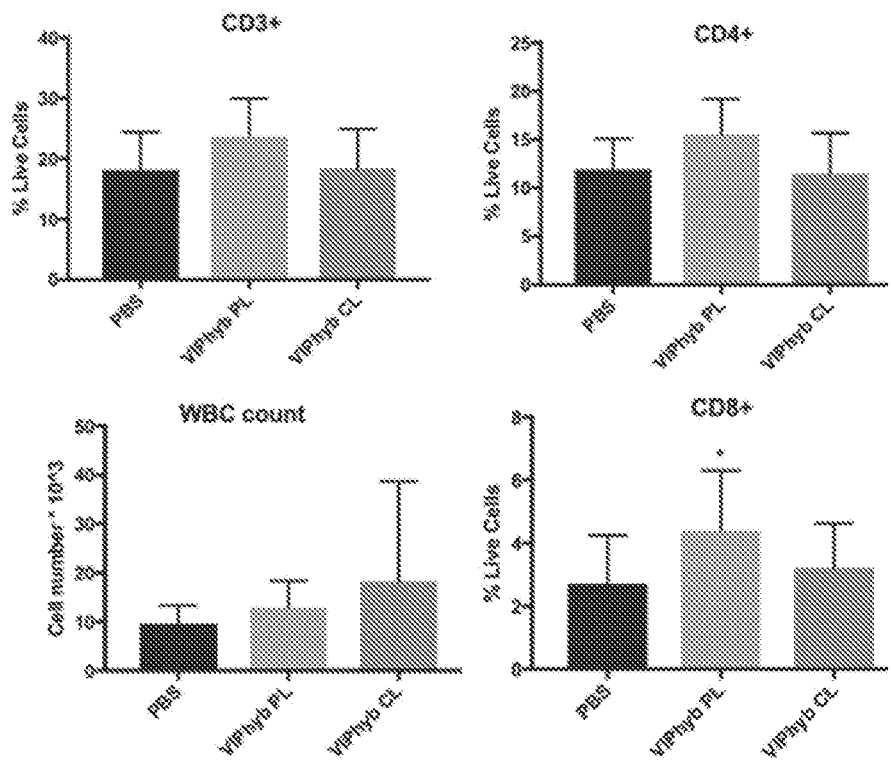
FIG. 1A shows data indicating VIPhyb Increased CD8+ T cell Proliferation. Frequency of CD3+, CD4+ and CD8+ T cells in the spleen and WBC count in peripheral blood upon euthanasia.
Figure 1B:
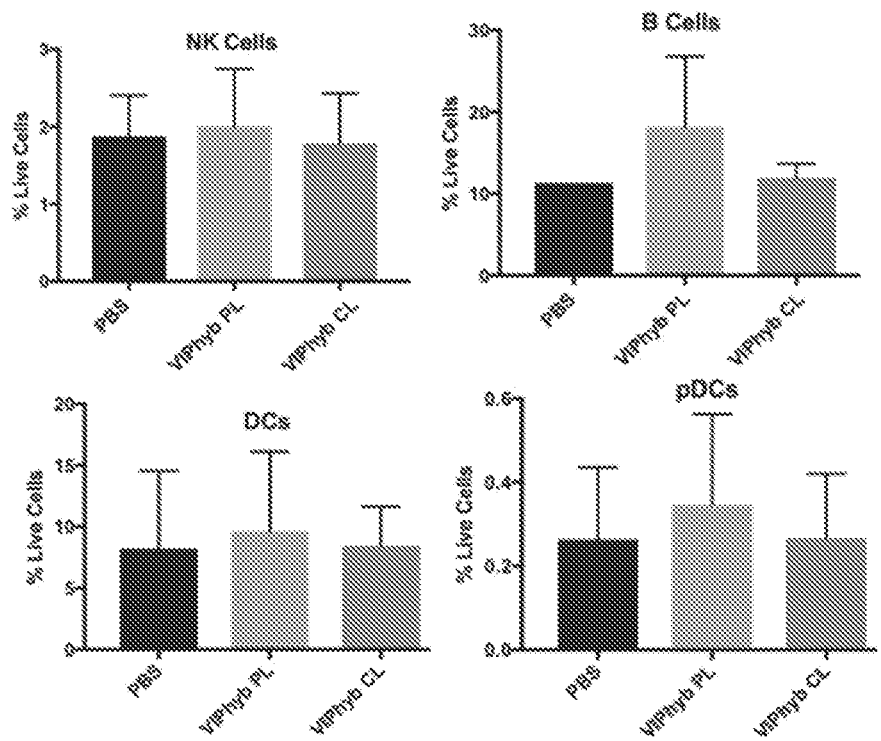
FIG. 1B shows data on the frequency of NK cells, B cells, dendritic cells, and plasmacytoid dendritic cells in the spleen upon euthanasia.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

The terms "vasoactive intestinal peptide" and "VIP" refer to (SEQ ID NO: 2) HSDAVFTDNYTRLRKQMAVK-KYLNSILN unless the context suggests otherwise. VIP is a multifunctional endogenous polypeptide that modulates both innate and adaptive immunity at multiple levels of immune cell differentiation and activation.

VIP is typically secreted by a variety of cells such as neurons (in both the central and peripheral nervous systems) B-cells, T-cells, and accessory cells. VIP and the closely related neuropeptide pituitary adenylyl cyclase-activating polypeptide (PACAP) bind to three known receptors-VPAC1, VPAC2, and PAC1. It is believed that T-cells and dendritic cells (DC) express VPAC1 and VPAC2, but not PAC1. PAC1 is mainly expressed on neuron and endocrine cells in the brain and pituitary and adrenal glands, and in most forms selectively binds PACAP.

The term "VIP antagonist" or "VIP receptor antagonist" refers to any molecule that inhibits or detracts from the ability of VIP to alter immune responses. VIP receptor antagonists are known including VIP analogues, VIP fragments, growth hormone-releasing factor analogous and hybrid peptides. A number of VIP receptor antagonists are disclosed in U.S. Pat. Nos. 5,565,424; 7,094,755; 6,828,304, and are all hereby incorporated by reference. Some examples of VIP receptor antagonist include [Ac-Tyr1,D-Phe2]GRF 1-29, amide, i.e., (SEQ ID NO: 4) YFDAIFTN-SYRKVLGQLSARKLLQDIMSR (Modifications: Tyr-1=N-terminal Ac, Phe-2=D-Phe, Arg-29=C-terminal amide); VIP (6-28), i.e., (SEQ ID NO:5) FTDNYTRLRKQMAVKKYLNSILN (Modifications: Asn-23=C-terminal amide); [D-p-Cl-Phe6, Leu17]-VIP, i.e., (SEQ ID NO:6) HSDAVFTDNYTRLRKQLAVKKYLN-SILN (Modifications: Phe-6=p-Cl-D-Phe, Asn=C-terminal amide); VIP-hyb also known as VIPhybrid (SEQ ID NO: 1) KPRRPYTDNYTRLRKQMAVKKYLNSILN, i.e., a hybrid peptide of neurotensin and VIP consisting of an N-terminal (SEQ ID NO:7) KPRRPY, also designated neurotensin (6-11)] followed by the C-terminal 22 amino acids of VIP, i.e., (SEQ ID NO:8) TDNYTRLRKQMAVKKYLNSILN, also designated VIP (7-28); N-terminal Stearyl, Norleucine 17 VIPhyb, i.e., (SEQ ID NO: 9) KPRRPY-TDNYTRLRKQXAVKKYLNSILN, wherein X is norleucine; Ac His1 [D-Phe(2), Lys(15), Arg(16), Leu(27)]-VIP (1-7)/GRF(8-27), i.e., (SEQ ID NO:10) HFDAVFTNSYRKVLKRLSARKLLQDIL, C-terminal amide; and pituitary adenylate cyclase-activating polypeptide, PACAP (6-38) C-terminal amide, i.e., (SEQ ID NO:11) TDSYSRYRKQMAVKKYLAAVLGKRYKQRVKNK. It is contemplated that any of these molecules may be modified with hydrocarbon or polyethylene glycol groups in order to provide improve properties such as solubility, bioavailability, and/or biological degradation.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Vasoactive Intestinal Peptide Antagonist Enhances T Cell Proliferation and Synergizes with PD-1 Antibodies to Promote Anti-Melanoma T cell Immune Responses Whether VIPhyb treatment would enhance T cell activation and cytotoxicity in response to melanoma, which can be highly immunogenic, was tested. VIPhyb synergistically enhanced T cell proliferation in vitro when combined with anti-PD1 antibodies. A dose-dependent enhancement of in vitro T cell proliferation in response to stimulation with anti-CD3 antibodies following the addition of VIPhyb was observed, along with reversal of the suppressive effect of exogenous VIP peptide on T cell proliferation.

To test the effect of blocking VIP-signalling on anti-cancer immune responses to solid tumors, mice bearing B16 melanoma tumors were treated with daily injections of VIPhyb. VIPhyb-treated mice had more effector CD8+ T cells compared with saline-treated controls, but single-agent VIPhyb treatment did not have a significant effect on the kinetics of tumor growth. Combining treatment with VIPhyb and PD-1 antibodies in mice with established melanoma significantly enhanced suppression of tumor growth and improved survival compared with mice treated with either inhibitor alone or saline-treated controls. VIPhyb- and anti-PD1 antibody treatment synergistically enhanced T cell mediated immunity as assessed by increased numbers of effector CD8+ T cells.

The greatest effects of VIPhyb, were seen when administered in mice in combination with a PD-1 inhibitor. Using monoclonal antibodies to reduce PD-1 signalling has profound effects on exhausted T cells in cancer and is currently FDA approved for treatment against melanoma in the clinic. This combination most likely affects CD8+ T cells most, as CD8+ T cells were increased both in a splenocyte co culture and in vivo experiments. Because PD-L1 expression on melanoma cells has been proven to be sufficient for immune evasion, T cells in mice treated only with VIPhyb may become anergic due to the upregulation of expression of PD-L1 on melanoma cells. Since CD8+ cytotoxic T cells are the primary effectors of an anti-tumor response, this validates the reduced tumor growth in combination treated mice. This concept would also explain the lack of splenocyte proliferation in vitro when VIPhyb is administered alone. As a result, when administered together, VIPhyb synergizes with PD-1 inhibition. Taken together, these data indicate that VIPhyb treatment alone does not affect tumor size, but bolsters CD8+ proliferation, an effect that is augmented in combination with a PD-1 inhibitor to reduce tumor burden and enhance survival.

The anticancer activity of treatment with VIPhyb appears to be T cell mediated. VIPhyb reversed exogenous VIP mediated splenic T cell suppression in vitro, suggesting that it may have the same effect on stimulating T cell expansion by antagonizing endogenous VIP in vivo. Further evidence for a T cell-mediated mechanism-of-action for VIPhyb is the absence of a direct effect on melanoma growth, invasiveness, and modulation of inhibitory surface molecules despite expression of VPAC2. Interestingly, a nanoparticle designed to target the tumor draining lymph nodes (TDLN) in mice, was able to stabilize the peptide in vitro leading to increased potency. Appropriately, the T cell stimulatory effect of VIPhyb was conserved with a VIPhyb-NP formulation, and was able to block the effects of exogenous VIP at higher concentrations. Thus, VIPhyb-NP may be more effective in activating an adaptive immune response in vivo than the free drug formulation.

Antagonizing the VIP pathway with VIPhyb results in significant enhancement of T cell growth in vitro and reduction of tumor growth while increasing survival as a combination therapy with a PD-1 monoclonal antibody. While the mechanism of how these drugs interact is a topic for future research, this synergistic effect supports the idea of blocking the VIP pathway as a therapeutic method in cancer immunotherapy.

Methods of Treating Cancer

In certain embodiments, this disclosure relates to methods of treating cancer or viral infections comprising administering an effective amount of a VIP antagonist in combination with an immune check-point inhibitor to a subject in need thereof. In certain embodiments, this disclosure relates to methods of treating or enhancing the immune response to cancer or viral infections comprising administering a VIP antagonist optionally conjugated to nanoparticles, in combination with an antibody to immune check-point molecules to a subject in need thereof.

In certain embodiments, the subject is diagnosed with a cancer selected from the group of melanoma, lung cancer, renal cancer, leukemia, non-Hodgkin's lymphoma, Hodgkin's lymphoma, myeloma, bladder cancer, pancreatic cancer, gastric cancer, esophageal cancer, glioblastoma, colon cancer, breast cancer and prostate cancer.

In certain embodiments, the antibody to immune check-point molecule is from the group of anti-PD1 antibodies including Pembrolizumab (Keytruda™) and Nivolumab (Opdivo™). In certain embodiments, the antibody to immune check-point molecule is from the group of anti-PDL1 antibodies including Atezolizumab (Tecentriq™), Avelumab (Bavencio), Durvalumab (Imfinzi™). In certain embodiments, the antibody to immune check-point molecule is Ipilimumab (Yervoy™).

In certain embodiments, the vasoactive intestinal polypeptide antagonist is composed of the sequence N Term KPRRPYTDNYTRLRKQMAVKKYLNSILN (SEQ ID NO: 1) C Term. In certain embodiments, the sequence of vasoactive intestinal polypeptide antagonist is modified to include a C-terminal link or composed of four glycines, a serine, and a terminal cysteine in order to facilitate coupling to the nanoparticle: N Term KPRRPY-TDNYTRLRKQMAVKKYLNSILNGGGGSC (SEQ ID NO: 3) C Term.

In certain embodiments, the VIP antagonist is selected from the group consisting of [Ac-Tyr1,D-Phe2]GRF 1-29, amide, i.e., (SEQ ID NO: 4) YFDAIFTNSYRKVLGQL-SARKLLQDIMSR (Modifications: Tyr-1=N-terminal Ac, Phe-2=D-Phe, Arg-29=C-terminal amide); VIP (6-28), i.e., (SEQ ID NO:5) FTDNYTRLRKQMAVKKYLNSILN (Modifications: Asn-23=C-terminal amide); [D-p-Cl-Phe6, Leu17]-VIP, i.e., (SEQ ID NO:6) HSDAVFTDNYTRLRKQLAVKKYLNSILN (Modifications: Phe-6=p-Cl-D-Phe, Asn=C-terminal amide); VIP-hyb also known as VIPhybrid (SEQ ID NO: 1) KPRRPY-TDNYTRLRKQMAVKKYLNSILN, i.e., a hybrid peptide of neurotensin and VIP consisting of an N-terminal (SEQ ID NO: 7) KPRRPY, also designated neurotensin (6-11)] followed by the C-terminal 22 amino acids of VIP, i.e., (SEQ ID NO:8) TDNYTRLRKQMAVKKYLNSILN, also designated VIP (7-28); N-terminal Stearyl, Norleucine 17 VIPhyb, i.e., (SEQ ID NO: 9) KPRRPY-TDNYTRLRKQXAVKKYLNSILN, wherein X is norleucine; Ac His1 [D-Phe(2), Lys(15), Arg(16), Leu(27)]-VIP (1-7)/GRF(8-27), i.e., (SEQ ID NO:10) HFDAVFTNSYRKVLKRLSARKLLQDIL, C-terminal amide; and pituitary adenylate cyclase-activating polypeptide, PACAP (6-38) C-terminal amide, i.e., (SEQ ID NO:11) TD SYSRYRKQMAVKKYLAAVLGKRYKQRVKNK.

In certain embodiments, the VIP antagonist is given by sub-cutaneous injection. In certain embodiments, the VIP antagonist is given by inhalation to deliver drug to the pulmonary alveoli. In certain embodiments, the VIP antagonist is administered by a hand-held delivery device driven with compressed gas. In certain embodiments, the VIP antagonist is dissolved in a solution of sterile saline and administered as an aerosol.

Cytotoxic T cells directly kill cells, and the response is antigen specific. In order to destroy tumors, cytotoxic cells must proliferate in sufficient numbers to overtake the dividing cancer cells. However, T cells are considered senescent if they have limited proliferative potential in response to antigenic stimulation. Filaci et al. report that a subset of effector T-cells, CD8+ CD28− T regulatory lymphocytes, inhibit T cell proliferative and cytotoxic functions in human cancers. J Immunol, 2007, 179: 4323-4334. Montes et al. indicate that tumors induce senescent T cells as a potential form of tumor immune evasion. Cancer Res, 2008, 68: 870-879. Senescent T cells are characterized by the loss of CD27 and CD28 expression, lack of proliferative capacity, and increased expression of senescence-associated molecules. See Ramello et al. Cell Death and Disease, 2014. 5, e1507. Thus, there is a need to identify improved methods of treating cancer by reversing senescence in T cells.

Magnetic beads coated with anti-CD3 and anti-CD28 (anti-CD3/CD28 beads) have been reported for the expansion of T cells that has been used experimentally to boost T cell immunity in immunosuppressed cancer patients. See Porter et al. A phase 1 trial of donor lymphocyte infusions expanded and activated ex vivo via CD3/CD28 costimulation. Blood, 2006, 107:1325-1331.

In certain embodiments, the disclosure contemplates methods of treating cancer or a chronic infection comprising: purifying T cells from a subject providing isolated T cells; mixing the isolated T cells with anti-CD3 antibodies and anti-CD28 antibodies optionally immobilized on a bead or solid surface in combination with a VIP receptor antagonist or nanoparticle thereof or combinations thereof; under conditions such that the T cells replicate providing replicated T cells have increased expression of CD28 compared with levels prior to replication; and administering an effective amount of the replicated T cells to a subject in need thereof in combination with an antibody to immune check-point molecules, anti-PD-1 antibodies or anti-PD-L1 antibodies.

In certain embodiments, the disclosure contemplates methods of treating cancer comprising: purifying T cells from a subject providing isolated T cells; mixing the isolated T cells with anti-CD3 antibodies and anti-CD28 antibodies optionally immobilized on a bead or solid surface in combination with a VIP receptor antagonist or nanoparticle thereof or combinations thereof; under conditions such that the T cells replicate providing replicated T cells have increased expression of CD28 compared with levels prior to replication; and administering an effective amount of the replicated T cells to a subject in need thereof in combination with antibody to immune check-point molecules, anti-PD-1 antibodies or anti-PD-L1 antibodies. In certain embodiments, the replicated T cells express a chimeric antigen receptor on the surface of the cells. In certain embodiments, the method further comprises administering a VIP receptor antagonist or nanoparticle thereof, or combinations thereof, before, during, or after administering the replicated T cells.

In certain embodiments, the disclosure contemplates method of treating cancer comprising: purifying T cells from a subject providing isolated T cells; culturing the isolated T cells by in vitro exposure of T cells to antibodies that bind CD3 and/or CD28 in combination with an agent or nanoparticle that prevents VIP from interacting with VIP receptors, e.g. prevents signalling through the VIP receptor and combinations thereof providing expanded T cells with an increased expression of CD28; and administering an effective amount of the replicated T cells to a subject in need thereof in combination with antibody to immune check-point molecules, anti-PD-1 antibodies or anti-PD-L1 antibodies.

In certain embodiments, the disclosure contemplates method of treating cancer comprising administering an effective amount of an antibody to immune check-point molecules, anti-PD-1 antibodies or anti-PD-L1 antibodies, a bi-specific antibody in combination with a VIP receptor antagonist or nanoparticle thereof to a subject in need thereof, wherein the bi-specific antibody comprises a cancer targeting binding sequence and a CD3 binding sequence. In certain embodiments, the bi-specific antibody is catumaxomab or blinatumomab.

In certain embodiments, the disclosure contemplates methods of treating cancer comprising administering an effective amount of an antibody to immune check-point molecules, anti-PD-1 antibodies or anti-PD-L1 antibodies in with a combination of bi-specific antibodies or anticancer antibody or antibody to a tumor associated antigen and administration or parental administration of a VIP receptor antagonist or nanoparticle thereof. In certain embodiments, the anti-tumor specific antibody is directed to CD19. In certain embodiments, the anti-cancer antibody is directed to CD123. In certain embodiments, the anti-cancer antibody is directed to HER2/neu. In certain embodiments, the anti-cancer antibody is directed to BMCA, a myeloma associated antigen. In certain embodiments, the anti-cancer antibody is directed to EGFR.

In certain embodiments, the disclosure contemplates methods of treating cancer comprising administering an effective amount of cells having a chimeric antigen receptor in combination with a VIP receptor antagonist or nanoparticle thereof in combination with an antibody to immune check-point molecules, anti-PD-1 antibodies or anti-PD-L1 antibodies to a subject in need thereof, wherein the chimeric antigen receptor comprises cancer targeting sequence, a transmembrane domain, a T cell costimulatory molecule domain, and a signal-transduction component of a T-cell antigen receptor domain.

In certain embodiments, this disclosure relates to methods of treating cancer comprising: purifying T cells from a subject that express a T cell receptor wherein the T cells express CD3 and optionally CD4 and/or CD8 providing isolated T cells; mixing the isolated T cells with cell culture disclosed herein under conditions such that the cells expand, and implanting or administering an effective amount of the expanded cells into the subject in combination with an antibody to immune check-point molecules, anti-PD-1 antibodies or anti-PD-L1 antibodies.

In certain embodiments, the disclosure contemplates methods of treating cancer comprising administering T cells comprising a vector configured to express a chimeric antigen receptor, e.g., the cells has been infected with a recombinant virus that has a nucleic acid that codes a chimeric antigen receptor, in combination with administration of a VIP receptor antagonist or nanoparticle thereof administering in combination with an antibody to immune check-point molecules, anti-PD-1 antibodies or anti-PD-L1 antibodies.

In certain embodiments, the disclosure contemplates methods of treating cancer comprising: purifying cells from a subject that express CD3 and/or CD4 and/or CD8 providing isolated T cells; measuring the expression of CD27 and/or CD28, on the isolated T cells providing measured values of CD27 and/or CD28; comparing the measured values of CD27 and/or CD28, to a reference level, and if the measured levels of CD27 are lower than normal and/or the measured levels of CD28 are lower than normal, then administering an effective amount of a VIP receptor antagonist or nanoparticle thereof in combination with an antibody to immune check-point molecules, anti-PD-1 antibodies or anti-PD-L1 antibodies to a subject.

In certain embodiments, the disclosure contemplates methods of treating cancer comprising purifying cells from a subject that express CD3 and/or CD4 and/or CD8 providing isolated T cells; measuring the expression of CD27 and/or CD28, on the isolated T cells providing measured values of CD27 and/or CD28; if the measured values of CD27 is lower than normal and/or the measured value of CD28 is lower than normal providing replicated T cells then mixing the isolated T cells with a VIP receptor antagonist or nanoparticle thereof or combinations thereof under conditions such that the isolated T cells replicate; and implanting or administering an effective amount of the replicated T cells into the subject optionally in combination with administering a VIP receptor antagonist or nanoparticle in combination with an antibody to immune check-point molecules, anti-PD-1 antibodies or anti-PD-L1 antibodies to the subject.

In certain embodiments, the disclosure relates to expanding T cells that are positive for CD3 and negative for CD4 and CD8 such as gamma delta T cells (γδ T cells). Gamma delta T cells that have a distinctive T-cell receptor (TCR) on their surface. Most T cells are αβ (alpha beta) T cells with TCR composed of two glycoprotein chains called α (alpha) and β (beta) TCR chains. In contrast, gamma delta (γδ) T cells have a TCR that is made up of one γ (gamma) chain and one δ (delta) chain.

In certain embodiments, the disclosure contemplates methods of treating cancer comprising: purifying and expanding T cells using methods provided herein providing isolated T cells; mixing the isolated T cells with bi-specific antibodies under conditions such that the bispecific antibodies bind the CD3-T cell receptor complex; and administering an effective amount of the bispecific antibody bound T cells to the subject in combination with administering a VIP receptor antagonist or nanoparticle in combination with an antibody to immune check-point molecules, anti-PD-1 antibodies or anti-PD-L1 antibodies to a subject in need thereof.

Bi-specific antibodies contain two targeting sequences, the first targets a tumor-associated antigen and the second targets the CD3 T-cell receptor complex such that T-cells can engage cancer cells. The Bi-specific antibody is linking the T cells to the cancer cells. See Zhukovsky et al. Bispecific antibodies and CARs: generalized immunotherapeutics harnessing T cell redirection, Current Opinion in Immunology, 2016, 40: 24-35. In certain embodiments, this disclosure contemplates that the bi-specific antibody is directed to the tumor-associated antigen, CD19 epitope, CD123, HER2/neu, or a BMCA, a myeloma associated antigen.

In order to improve the ability of immune cells to kill cancerous cells, T cells can be isolated from the blood of a patient and genetically altered to express chimeric antigen receptors to specifically target proteins expressed on the surface of cancerous cells and stimulate an immune response. When put back into the patient, the cells attack the cancerous cells. In certain embodiment, this disclosure contemplates using CAR T cells that target the CD22 and/or CD19 antigens. CD19 is a protein expressed on cancerous B cells. Brentjens et al. report that T cells altered to bind CD19 can induce remissions of cancer in adults with chemotherapy-refractory acute lymphoblastic leukemia. Sci Transl Med, 2013, 5(177):177ra38.

In a typical procedure, T cells are purified and isolated from blood or bone marrow. For example, T cells are collected via apheresis, a process that withdraws blood from the body and removes one or more blood components (such as plasma, platelets or other white blood cells). The remaining blood is then returned back into the body. The cells are exposed to a recombinant vector, such as a lentiviral vector, that infects the cells in a way that a CAR protein is produced to be present in the cell membrane. The T cells may be sent to a laboratory or a drug manufacturing facility where they are genetically engineered to produce chimeric antigen receptors (CARs) on their surface. Before and/or after infecting the isolated cells with the recombinant vector, the cells may be induced to replicate using methods disclosed herein. The genetically modified T cells may be expanded by growing cells in the laboratory until there are sufficient number of them. Optionally, these CAR T cells are frozen. The modified cells are then administered back to the patient. In certain embodiments, this disclosure contemplates that the subjects are administered with a VIP receptor antagonist or nanoparticle thereof optionally in combination with one or more chemotherapy agent or nanoparticles before they receive the infusion of CAR T cells.

In certain embodiments, the disclosure relates to cells made by processes disclosed herein that contain recombinants vector comprising a nucleic acid that encodes a chimeric polypeptide comprising a targeting sequence, a transmembrane domain, a T cell costimulatory molecule domain, and a signal-transduction component of a T-cell antigen receptor domain.

In certain embodiments, the targeting sequence in a chimeric antigen receptor refers to any variety of polypeptide sequences capable of selectively binding to a surface protein on target cells, e.g., cancer cells. Other targeting sequences may be variable binding regions of antibodies, single chain antibodies, and antibody mimetic. In certain embodiments, targeting is achieved via a single-chain variable fragment (scFv) derived from a monoclonal antibody. The targeting sequence it typically connected to the intracellular domains by a hinge/transmembrane region, commonly derived from CD8 or IgG4. The intracellular domains may contain co-stimulatory domains such as 4-1BBzeta and/or CD28zeta linked to the cytoplasmic signalling domain of CD3zeta.

Methods of Treating Viral Infections

In certain embodiments, this disclosure contemplates treating a viral infection comprising administering an effective amount of VIP receptor antagonists or nanoparticle thereof optionally in combination with an antibody to immune check-point molecules, anti-PD-1 antibodies or anti-PD-L1 antibodies to a subject in need thereof. In certain embodiments, the subject is diagnosed with an active or inactive chronic viral infection.

In certain embodiments, this disclosure contemplates methods of treating an active viral infection comprising administering an effective amount of a VIP receptor antagonists or nanoparticle thereof, optionally in combination with an antibody to immune check-point molecules, anti-PD-1 antibodies or anti-PD-L1 antibodies, to a subject diagnosed with and exhibiting signs or symptoms of an active chronic viral infection. In certain embodiments, a titer of virus in the subject is reduced after administering the vasoactive intestinal peptide antagonist as compared to pre-treatment.

In certain embodiments, a VIP receptor antagonists or nanoparticle thereof, optionally in combination with an antibody to immune check-point molecules, anti-PD-1 antibodies or anti-PD-L1 antibodies, and cells are administered or transplanted into the subject. In certain embodiments, the cells are selected from the group consisting of autologous or allogeneic T-cells, allogeneic cells from a HLA matched donor, or allogeneic cells from a HLA mis-matched donor. In certain embodiments, the cell is a bone marrow cell. In certain embodiments, the cell is a blood mononuclear cell comprising/expressing granulocyte colony-stimulating factor. The cell therapy may be conducted with non-mobilized blood mononuclear cells.

In certain embodiments, the cells are T-cells activated by CD3/CD28 co-stimulation. In certain embodiments, the activated T-cells are infused into a patient with chronic CMV infection. In certain embodiments, the activated T-cells are infused into a patient with chronic EBV infection. In certain embodiments, the activated T-cells are infused into a patient with chronic BK virus infection. In certain embodiments, the activated T-cells are infused into a patient with chronic adenovirus infection.

In certain embodiments, the disclosure relates to methods of treating or preventing a viral infection comprising administering VIP receptor antagonists or nanoparticle thereof, optionally in combination with an antibody to immune check-point molecules, anti-PD-1 antibodies or anti-PD-L1 antibodies, to a subject in need thereof to a subject at risk of, exhibiting symptoms of, or diagnosed with a viral infection. In certain embodiments, the subject is immune compromised or the subject is an allogeneic bone marrow transplant donor or recipient. In typical embodiments, the subject is an organ transplant recipient, undergoing hemodialysis, diagnosed with cancer, receiving an immunosuppressive drug, and/or diagnosed with an HIV-infection. In certain embodiments, the disclosure relates to preventing a viral infection in an immunocompromised subject at risk of infection by administering a VIP antagonist and optionally one or more antiviral agents.

In some embodiments, the disclosure relates to the use of VIP receptor antagonists or nanoparticle thereof, optionally in combination with an antibody to immune check-point molecules, anti-PD-1 antibodies or anti-PD-L1 antibodies, in the production of an anti-viral medicament for the treatment of a viral infection.

In some embodiments, the subject is diagnosed with a chronic viral infection. In certain embodiments, the subject undergoes serological monitoring. In some embodiments, the administration is under conditions such that the viral infection is no longer detected. In some embodiments, the subject is diagnosed with a RNA virus, DNA virus, or retroviruses. In some embodiments, the subject is diagnosed with a virus that is double stranded DNA virus, sense single stranded DNA virus, double stranded RNA virus, sense single stranded RNA virus, antisense single stranded RNA virus, sense single stranded RNA retrovirus or a double stranded DNA retrovirus. In some embodiments, the subject is diagnosed to have a rotavirus, an influenza virus, a herpes virus, a hepatitis virus, or a lentivirus. In some embodiments, titer of the virus in the subject is reduced after the treatment as compared to pre-treatment.

In some embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In some embodiments, the disclosure relates to treating or preventing a viral infection by administering VIP receptor antagonists or nanoparticle thereof, optionally in combination with an antibody to immune check-point molecules, anti-PD-1 antibodies or anti-PD-L1 antibodies, in combination with a second antiviral agent. In further embodiments, the subject is co-administered with abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, Imunovir™, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu™), peginterferon alfa-2a, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, Truvada™, valaciclovir (Valtrex™), valganciclovir, vicriviroc, vidarabine, viramidine zalcitabine, zanamivir (Relenza™), and/or zidovudine. In certain embodiments, the subject is administered a pharmaceutical composition comprising VIP receptor antagonists or nanoparticle thereof optionally in combination with an antibody to immune check-point molecules, anti-PD-1 antibodies or anti-PD-L1 antibodies and a second antiviral agent.

In certain embodiments, the disclosure relates to treating or preventing a viral infection by administering a VIP receptor antagonists or nanoparticle thereof optionally in combination with an antibody to immune check-point molecules, anti-PD-1 antibodies or anti-PD-L1 antibodies, and a viral vaccine or in the absence of a viral vaccine.

In certain embodiments, the disclosure relates to enhancing the immune response to a vaccine comprising administering a VIP antagonist to a subject in need thereof. Typically, the vaccine is selected from the group of vaccines consisting of herpes zoster vaccine, smallpox vaccine, polio vaccine, pertussis vaccine, influenza vaccine, diphtheria vaccine, tetanus vaccine, meningococcus vaccine, influenza A vaccine including subtype H1N1 vaccine, influenza B vaccine, influenza C vaccine, rotavirus A vaccine, rotavirus B vaccine, rotavirus C vaccine, rotavirus D vaccine, rotavirus E vaccine, SARS coronavirus vaccine, human adenovirus types (HAdV-1 to 55) vaccine, human papillomavirus (HPV) vaccine, parvovirus B19 vaccine, molluscum contagiosum vaccine, JC vaccine, BK vaccine, Merkel cell polyomavirus vaccine, coxsackie A vaccine, norovirus vaccine, Rubella vaccine, lymphocytic choriomeningitis vaccine, yellow fever vaccine, measles vaccine, mumps vaccine, respiratory syncytial vaccine, rinderpest vaccine, California encephalitis vaccine, hantavirus vaccine, rabies vaccine, ebola vaccine, marburg vaccine, herpes simplex virus-1 (HSV-1) vaccine, herpes simplex virus-2 (HSV-2) vaccine, varicella zoster vaccine, Epstein-Barr virus (EBV) vaccine, cytomegalovirus (CMV) vaccine, herpes lymphotropic vaccine, roseolovirus vaccine, Kaposi's sarcoma-associated herpesvirus vaccine, hepatitis A (HAV) vaccine, hepatitis B (HBV) vaccine, hepatitis C (HCV) vaccine, hepatitis D (HDV) vaccine, hepatitis E (HEV) vaccine, human immunodeficiency virus (HIV) vaccine, The Human T-lymphotropic virus Type I (HTLV-1) vaccine, Friend spleen focus-forming virus (SFFV) vaccine, and Xenotropic MuLV-Related Virus (XMRV) vaccine. In certain embodiments, the vaccine for a subject diagnosed with a chronic viral infection.

Pharmaceutical Compositions

In certain embodiments, the disclosure contemplates pharmaceutical composition comprising a VIP receptor antagonist or nanoparticle thereof, or optionally other pharmaceutical agent, or pharmaceutically acceptable salts thereof, and a pharmaceutically acceptable excipient. In certain embodiments, the pharmaceutical composition is in the form of a sterilized pH buffered aqueous salt solution. In certain embodiments, the pharmaceutically acceptable excipient is aerosolizing agent or phospholipids. In certain embodiments, the aerosolizing agent is a hydrofluoroalkane, 1,1,1,2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof. In certain embodiments, the phospholipid is dipalmitoylphosphatidylcholine, palmitoyl-oleoyl phosphatidylglycerol, phosphatidylglycerol, or combinations thereof.

In certain embodiments, the pharmaceutical compositions may be stored in a nebulizer, inhaler, or other container optionally sealed or under a pressure for propelling the pharmaceutical agent(s). The container may contain a spraying apparatus that is manually-actuated or pressurized. Metered dose inhalers (MDIs) typically have a handheld aerosol canister that, upon being pushed, releases an amount of medicine to inhale. Dry powder inhalers (DPIs) do not use a propellant to release the medicine. Instead, a dry powder form of the VIP receptor antagonist or nanoparticle thereof or agent is drawn into your lungs after a breath. In certain configurations, a container comprising the VIP receptor antagonist or nanoparticle thereof, or agent is inserted a device. Pressing a button or section on the device pierces the container. One can breathe in the powder contained in the container through a mouthpiece on the device.

In certain embodiments, the pharmaceutical compositions may contain naturally or non-naturally occurring pulmonary surfactant compositions. Contemplated natural pulmonary surfactant compositions typically comprise 70-90% phospholipids (PC) such as dipalmitoylphosphatidylcholine (DPPC), phosphatidylcholine, and phosphatidylglycerol (PG); and 1-10% surfactant-associated proteins, apolipoproteins SP-A (SFTPA1), B (SFTPB), C (SFTPC) and D (SFTPD) (SP standing for "surfactant-associated protein"); and 1-10% Cholesterol (neutral lipids). Artificial pulmonary surfactants include colfosceril palmitate (Exosurf), a mixture of DPPC with hexadecanol and tyloxapol added as spreading agents; pumactant (Artificial Lung Expanding Compound or ALEC), a mixture of DPPC and PG; KL-4, composed of DPPC, palmitoyl-oleoyl phosphatidylglycerol, and palmitic acid, combined with a 21 amino acid synthetic peptide that mimics the structural characteristics of SP-B; and Venticute™, composed of DPPC, PG, palmitic acid and recombinant SP-C shares a nearly identical sequence with human SP-C except that the palmitoylated cysteines are absent and have been replaced with phenylalanines to eliminate protein oligomerization. Contemplated animal derived surfactants include beractant (Alveofact™), extracted from cow lung lavage fluid and (Survanta™), extracted from minced cow lung with additional DPPC, palmitic acid and tripalmitin; calfactant (Infasurf™), extracted from calf lung lavage fluid; and poractant alfa (Curosurf™)—extracted from material derived from minced pig lung.

In certain embodiments, the pharmaceutical compositions disclosed herein further comprise a respiratory agent selected from a glucocorticoid receptor agonist (steroidal and non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, alclometasone dipropionate; a p38 antagonist such as losmapimod; a phosphodiesterase (PDE) inhibitor such as a methylxanthine, theophylline, and aminophylline; a selective PDE isoenzyme inhibitor, a PDE4 inhibitor and the isoform PDE4D, such as tetomilast, roflumilast, oglemilast, ibudilast, ronomilast; a modulator of chemokine receptor function such as vicriviroc, maraviroc, cenicriviroc, navarixin; a leukotriene biosynthesis inhibitor, 5-lipoxygenase (5-LO) inhibitor, and 5-lipoxygenase activating protein (FLAP) antagonist such as TA270 (4-hydroxy-1-methyl-3-octyloxy-7-sinapinoylamino-2(1H)-quinolinone) such as setileuton, licofelone, quiflapon, zileuton, zafirlukast, or montelukast; and a myeloperoxidase antagonist such as resveratrol and piceatannol.

Effective doses may be extrapolated from dose-response curves derived from in vitro or animal model test systems. For a VIP receptor antagonist or nanoparticle thereof or other agents, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Further, the dosage and frequency of administration of a VIP receptor antagonists or nanoparticle thereof or agent may be reduced by enhancing uptake and tissue penetration by modifications such as, for example, lipidation and the inclusion of natural or artificial pulmonary surfactants.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. In certain embodiments, the pharmaceutical compositions contain a pharmaceutically acceptable excipient that is a solubilizing agent such as a lipid, cholesterol, fatty acid, fatty acid alkyl ester, linoleic acid, oleic acid arachidonic acid, saccharide, polysaccharide, cyclodextrin, 2-hydoxypropyl(cyclodextrin), or combinations thereof.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, the pharmaceutical compositions is in solid form surrounded by an enteric coating, i.e., a polymer barrier applied on oral medication that prevents its dissolution or disintegration in the gastric environment. Compounds typically found in enteric coatings include methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, and combinations thereof.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be both natural and artificial pulmonary surfactants, sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with a VIP receptor antagonist or nanoparticle thereof or agents disclosed herein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiment, this disclosure contemplates pharmaceutical compositions comprising a VIP receptor antagonist or nanoparticle thereof, and agents disclosed herein and pharmaceutically acceptable excipient. In certain embodiments, this disclosure contemplates the production of a medicament comprising VIP receptor antagonists or nanoparticles thereof or agents disclosed herein and uses for methods disclosed herein.

In certain embodiments, the disclosure relates to pharmaceutical compositions comprising VIP receptor antagonists or nanoparticles thereof, and agents disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and Viscoleo™), preparations incorporated into pulmonary surfactants (both natural and artificial), and injectable organic esters such as ethyl oleate.

Prevention of the action of microorganisms may be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminium monostearate and gelatin.

Solid dosage forms for oral administration include capsules, tablets, pills, powders and granules. In such solid dosage forms, the VIP receptor antagonists or nanoparticles thereof, or agents may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the a VIP receptor antagonists or nanoparticles thereof and agents, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

In certain embodiments, production processes are contemplated which two components, a VIP receptor antagonist or nanoparticle thereof and agents disclosed herein and a pharmaceutical carrier, are provided already in a combined dry form ready to be reconstituted together. In other embodiments, it is contemplated that a VIP receptor antagonist or nanoparticle thereof and agents disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the coated a VIP receptor antagonist or nanoparticle thereof, or agents can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as inhalers, syringes, vials, tubes, etc. The pharmaceutical composition may then be applied via actuation or specific needles of the syringe or via suitable catheters. A typical diluent comprises water for injection, and NaCl (preferably 50 to 150 mM, especially 110 mM), $CaCl_2$ (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, this disclosure contemplates a kit comprising a pharmaceutical composition disclosed herein such as a VIP receptor antagonist or nanoparticle thereof or agent and a container optionally with a suitable diluent. Further components of the kit may be instructions for use, administration means, such as inhalers, syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

Antibodies

In certain embodiments, the VIP antagonist is a VIP antibody or antibody fragment to VIP or a VIP receptor. In certain embodiments, the disclosure relates to a pharmaceutical composition comprising a VIP antibody, or antibody fragment, and a pharmaceutically acceptable excipient. In certain embodiments, the disclosure relates to pharmaceutical composition comprising a VIP receptor antibody, or antibody fragment, and a pharmaceutically acceptable excipient.

The disclosure also includes relates to a VIP antagonist antibody that specifically binds VIP or VIP receptor such as VPAC1, VPAC2, and PAC1. The disclosure should not be construed as being limited solely one type of antibody. Rather, should be construed to include antibodies that specifically bind VIP, VIP preproproteins, VIP receptors, or portions thereof. One skilled in the art would appreciate, based upon the disclosure provided herein, that the antibody can specifically bind with any portion of the polypeptide and the polypeptide can be used to generate antibodies specific. However, in certain embodiments, the disclosure is not limited to using the full-length polypeptide corresponding to VIP.

The antibodies can be produced by immunizing an animal such as, but not limited to, a rabbit or a mouse, with a protein, or a portion thereof, or by immunizing an animal using a protein comprising at least a portion of the polypeptide corresponding to VIP. One skilled in the art would appreciate, based upon the disclosure provided herein, smaller fragments of these proteins can also be used to produce antibodies that specifically bind the polypeptide.

Certain embodiments of the disclosure encompass polyclonal, monoclonal, synthetic antibodies, and the like. Moreover, the antibody can be used to detect and or measure the amount of protein present in a biological sample using well-known methods such as, but not limited to, Western blotting and enzyme-linked immunosorbent assay (ELISA). The antibody can also be used to immunoprecipitate and/or immuno-affinity purify their cognate antigen using methods well-known in the art. Thus, by administering the antibody to a cell or to the tissue of an animal, or to the animal itself, the interactions between VIP and its cognate receptor are therefore inhibited.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See, e.g., U.S. Pat. Nos. 4,816,567 and 4,816,397. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An VIP antibody or antibody fragment thereof may also be modified by specific deletion of human T cell epitopes or "deimmunization" by the methods disclosed in U.S. Pat. Nos. 7,125,689 and 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition, a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Nanoparticles Conjugated with an Antagonist for Vasoactive Intestinal Peptide

In certain embodiments, this disclosure relates to VIP antagonists, optionally conjugated to nanoparticles, for use in methods of treating cancer. In certain embodiments, this disclosure relates to methods of treating or enhancing the immune response to cancer or viral infections comprising administering a VIP antagonist, optionally conjugated to nanoparticles, in combination with an immune check-point inhibitor, e.g, antibody to immune check-point molecules, to a subject in need thereof.

Vasoactive intestinal peptide (VIP) is an immunosuppressive neuropeptide that leads to reduced T cell proliferation and reduced production of pro-inflammatory cytokines. Thus, blockade of the VIP pathway as a therapeutic target, results in a robust immune response. VIPhyb, a peptide antagonist of VIP, increases the number of effector/memory CD8+ T cells and mature NK cells. Further, VIPhyb down regulates the expression of PD-1 and PD-L1 in activated T cells and dendritic cells, respectively.

VIPhyb, KPRRPYTDNYTRLRKQMAVKKYLN-SILNGGGGSC (SEQ ID NO: 3) is conjugated to a 30 nm Pluronic-stabilized polypropylene sulfide nanoparticle (VIPhyb-NP) (See Schudel et al S-nitrosated polypropylene sulfide nanoparticles, Adv. Healthcare Mater. 2015, 4, 1484-1490).

In certain embodiments, the nanoparticle has a diameter of between 10 and 100 nm. In certain embodiments, the nanoparticle has a diameter between 20 and 50 nm, preferably 30 nm. In certain embodiments, the antagonist of vasoactive intestinal polypeptide signalling contains the peptide sequence of VIPhyb, KPRRPY-TDNYTRLRKQMAVKKYLNSILN (SEQ ID NO: 1). In certain embodiments, the disclosure contemplates using particles disclosed herein when the peptide sequence couple to the nanoparticle is contains VIPhyb plus a C-terminal linker peptide, KPRRPYTDNYTRLRKQMAVKKYLN-SILNGGGGSC (SEQ ID NO: 3). In certain embodiments, the molar ratio of antagonist peptide to the nanoparticles is about 60 to one nanoparticle or between 40 and 70 to one nanoparticle.

In certain embodiments, the VIP antagonist is coupled to a nanoparticle thereby improving the half-life of the vasoactive intestinal polypeptide in the alveolar space. In certain embodiments, the nanoparticle is 20 to 40 nanometers in size. In certain embodiments, the nanoparticle is composed of biodegradable and biocompatible polyethylene glycol.

In certain embodiments, this disclosure relates to methods of coupling a chemical antagonist of vasoactive intestinal polypeptide signalling to a nanoparticle. In certain embodiments, the nanoparticle is comprised of Pluronic-stabilized polypropylene sulfide. In certain embodiments, the chemical linkage between the VIP antagonistic peptide and the nanoparticles is a disulfide bond. In certain embodiments, the nanoparticle comprises disulphide linked polymer wherein the VIP antagonist is linked to the nanoparticle through a disulphide bond of a C-terminal cysteine. In certain embodiments, the nanoparticle comprises a core comprising disulphide linked polymer with a polyethylene glycol coating.

In certain embodiments, nanoparticles comprising a VIP antagonist disclosed herein is 20 to 40 nanometers in diameter. In certain embodiments, the nanoparticle is composed of biodegradable and biocompatible polyethylene glycol. In certain embodiments, sequence of vasoactive intestinal polypeptide is modified to include a C-terminal link or composed of four glycines, a serine, and a terminal cysteine in order to facilitate coupling to the nanoparticle.

In certain embodiments, this disclosure relates to methods of augmenting T-cell activation and ex vivo expansion by co-incubation of human T cells with a nanoparticle containing a small molecule antagonist of VIP signalling, e.g., mixing T cells with nanoparticles disclosed herein.

EXAMPLES

VIPhyb Alone has No Effect on B16F1 Tumor Growth and Survival

Syngeneic transplantation models involve the induction and transplantation of melanoma cells into the same species and genetic background. This model is especially helpful in studying melanoma immunology, as it allows for the interaction of melanoma cells with competent T cells and B-cells found naturally in the human melanoma microenvironment. A handful of cell lines are utilized in melanoma syngeneic transplantation models such as Harding-Passey, Cloudman S91, and B16.

B16 was derived from a spontaneously arising melanoma of C57BL/6J origin, and has diverse subclones with different propensities for proliferation, invasion, and metastasis1. Two well-established subclones of the B16 melanoma cell line include B16F1 and B16F10. B16F1 demonstrates a low metastatic potential and is useful for studying primary tumor growth. B16F10, however, has a high metastatic potential, especially to the lungs, and is ideal for in vivo studies because of its rapid growth pattern and high turnover. Upon subcutaneous injection, B16 will form a palpable tumor in 5 to 10 days and grow to a 1 cm×1 cm tumor in 14 to 21 days. If grown larger, the tumors can become necrotic in the center, and begin to ulcerate or bleed.

Efficacy of immunotherapies against B16 is thought to be a reasonable predictor of the performance of immune therapies against human tumors. B16 melanoma is poorly immunogenic, as it expresses low levels of MHC1, limiting their ability to be recognized by cytotoxic CD8+ T cells. However, they express high levels of other targetable melanoma-associated antigens like tyrosinase related protein 2 (TRP-2) or gp100. Viral, DNA, dendritic cell, whole-tumor, and peptide vaccination regimens tested against established, palpable B16 tumors, reflects the response seen in the clinic. As a result, it is possible to generate potent anti-tumor immune responses against these tumors when the therapy generates large T cell responses.

To investigate VIPhyb as an immunotherapy for melanoma, and to determine the best route of administration, Luciferase-expression B16F1 cells were injected into B6 Albino syngeneic recipients and given 10 μg of VIPhyb peritumorally or subcutaneously on the contralateral flank beginning 1 day before tumor inoculation and continuing daily until the experimental endpoint. Mice were monitored for tumor growth and survival, and no difference in tumor burden was found between the two different routes of administration. The data indicated no significant change in tumor volume between the treated and untreated mice as measured twice weekly with digital calipers. In addition, there was no significant difference in survival. This nonsignificant effect on tumor volume was supported with once weekly bioluminescent imaging to quantify the overall tumor burden, showing no tumor reduction in the VIPhyb treated mice.

VIPhyb Enhances CD8+ T Cell Proliferation

Whether VIPhyb has an effect on adaptive immunity was testes. Mice with tumors that exceeded 500 $mm^3$ in volume were euthanized and their splenocytes phenotyped using flow cytometry. Blood was also collected for a complete blood count (CBC) to determine amount of peripheral white blood cells (WBCs). Of particular interest was the expansion of CD8+ T cells to corroborate the in vitro data, and expression of the inhibitory molecule PD-1. Though there was a nonsignificant modest increase in CD4+ T cells and peripheral WBCs, there were significantly more CD8+ T cells from VIPhyb-treated mice injected peritumorally (FIG. 1A). Further, there was a nonsignificant increase in NK cells, B cells, and different dendritic cell subtypes (FIG. 1B). the functional capacity of T cells from the spleens of VIPhyb and PBS-treated B16F1-bearing mice was analysed by intracellular cytokine staining. There was no significant difference in the frequency of IFNγ, TNF, Granzyme B, and IL-2-producing cells in both the CD4+ and CD8+ compartments comparing VIPhyb treated mice with PBS treated controls. Further, there was no significant difference in the frequency of CD4+ and CD8+ T cells expressing the PD-1, CTLA-4, and Lag-3 co-inhibitory ligands.

VIPhyb Alone does not Enhance Splenocyte Proliferation and T Cell Expansion in a B16F1 and B16F10 Co Culture Unless Combined with an Anti-PD-1 Antibody Whether combination of a VIPhyb with a PD-1 inhibitor could enhance an adaptive immune response to the more aggressive B16F10 model in vitro was investigated. Therefore, irradiated B16F1 and B16F10 cells were co-cultured with luciferase expressing splenocytes from B6 mice. Cells were placed in 96-well plates pre-coated with anti-CD3 antibody and low-dose recombinant murine IL-2 for 3 days and assessed proliferation by BLI. Administration of VIPhyb was not enough to promote expansion of splenocytes. However, when added with 1 dose of 10 μg of anti-PD-1 antibody, splenocyte proliferation increased dose-dependently (FIG. 2A). Data on proliferation of the cytotoxic CD4+ T cells and CD8+ T cells subsets when co-cultured with B16F10 are shown in FIGS. 2B and 2C.

VIPhyb Synergizes with an Anti-PD-1 Antibody to Reduce Tumor Burden

Figure 3A:
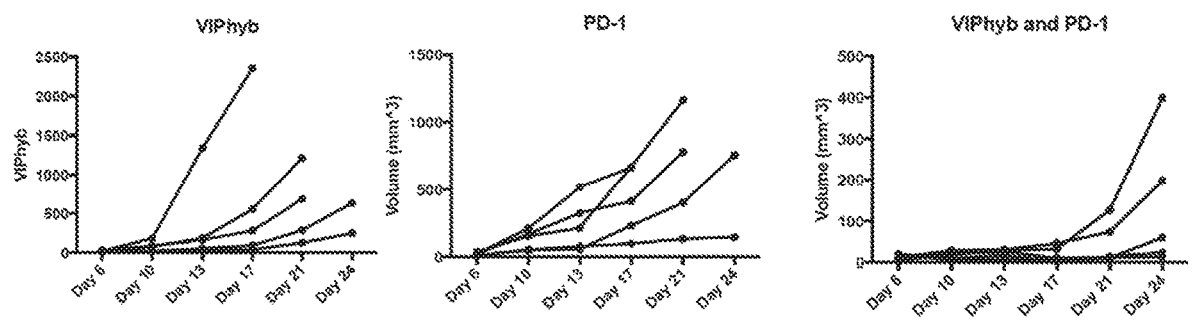
FIG. 3A shows data indicating VIPhyb Synergizes with an anti-PD-1 antibody significantly reducing B16F10 tumor growth. Tumor volumes were calculated as (length*width)/2.
Figure 3B:
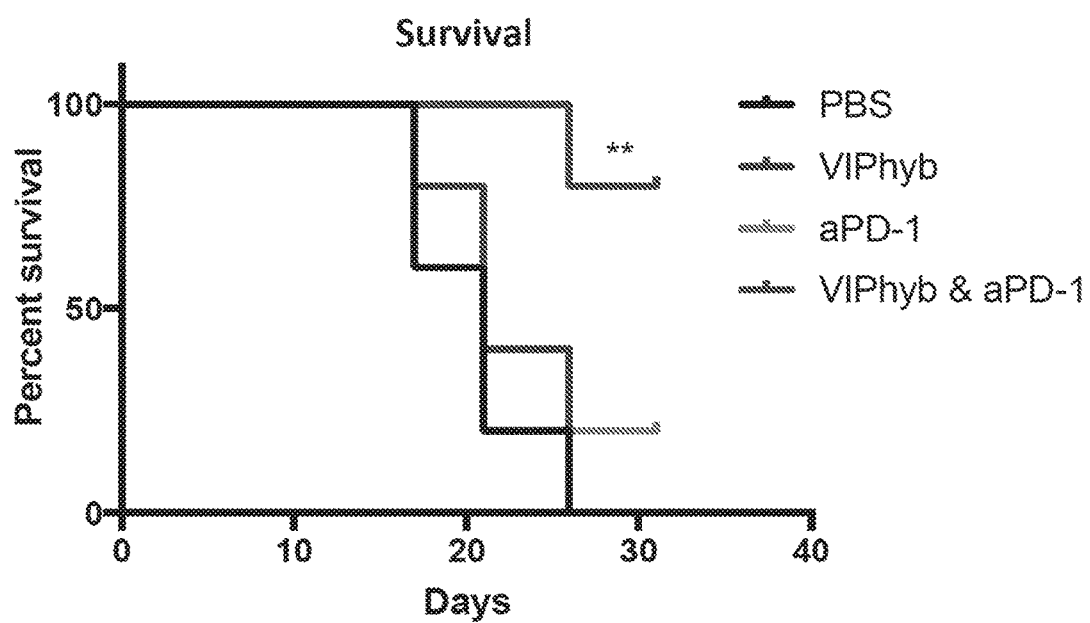
FIG. 3B shows survival data. B16F10 cells bearing, VIPhyb-treated, PD-1 treated, and both VIPhyb and PD-1 treated B6 Albino mice, compared with B16F10 bearing, PBS treated mice through day 25.
Figure 6A:
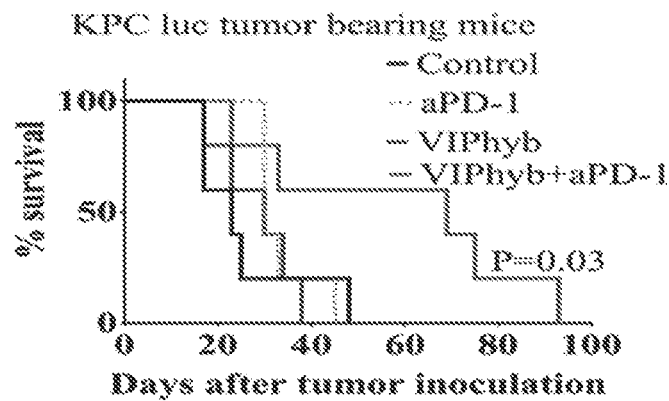
FIG. 6A shows data indicating prolonged survival and increased CD8+ T cell infiltration in mice treated with a combination of VIPhyb and anti-PD1 antibody. Mice were subcutaneously injected with KPC luc cells and treated with VIPhyb and/or anti-PD1 after the tumors were palpable. The tumors were monitored and the mice were sacrificed when the tumor volumes reached 500 mm$^3$. Survival curve shows significantly improved survival in mice treated with a combination of VIPhyb and anti-PD1.

Because VIPhyb alone did not activate a robust anti-tumor immune response in a B16F1 tumor model, whether a combination with an anti-PD-1 antibody in the B16F10 model would stimulate a synergistic effect was tested. B16F10 cells were injected into B6 Albino mice. VIPhyb (10 μg) was administered subcutaneously every day for 10 days. Three doses of 200 μg of an PD-1 antibody was intraperitoneally administered every 3 days. A combination both VIPhyb and the PD-1 antibody were also administered. FIG. 6A shows the tumor growth through day 17 of the in vivo experiments. B16F10-bearing mice treated with VIPhyb or an aPD-1 antibody have a lower average tumor volume than untreated B16F10-bearing mice. However, mice treated with a combination of VIPhyb and an aPD-1 antibody had a significantly lower tumor volume on average (FIG. 3A) and increased survival (FIG. 3B).

VIPhyb Regenerates Functional Immunity in Pancreatic Ductal Adenocarcinoma

Analysis of the cancer genome atlas (TCGA) data, it was discovered that PDAC has elevated mRNA expression of vasoactive intestinal peptide (VIP), a neurotransmitter, commonly associated with gut motility and blood pressure. VIP has immunosuppressive properties, such as decreasing T cell proliferation, polarizing T cells towards Th2 phenotype and increasing the frequency of immunosuppressive cells such as myeloid derived suppressor cells (MDSCs) and regulatory T cells (Tregs). Preliminary data also revealed that peripheral blood of PDAC patients have elevated levels of secreted VIP when compared to healthy volunteers. Likewise, murine PDAC also secreted exceptionally high levels of VIP both in-vitro and in-vivo, when compared to other cancers such as breast cancer.

Experiments were performed to determine if in PDAC, elevated VIP levels are promoting an immunosuppressive tumor microenvironment (TME) reducing the likelihood of effective T cell infiltration, and whether inhibiting VIP signaling will thereby regenerate the functional immunity in PDAC and render it more responsive to immunotherapy.

The antagonist of VIP signaling (VIPhyb) was used in two murine models of PDAC, namely MT5 and KPC. The KPC cell lines were transfected with luciferin, which further enabled us to visually monitor the tumor growth via bioluminescent imaging. After subcutaneous injection of either cell line, tumor growth was monitored when one administered anti-PD1 or VIPhyb or a combination of both (VIPhyb+anti-PD1) to mice with palpable tumors. The mice in the combination group in both MT5 and KPC PDAC model had significantly increased tumor free survival with 20% of mice remaining tumor free in the MT5 model and significantly delayed tumor progression in KPC model. Furthermore, analysis of the tumor tissue sections revealed that the combination group had enhanced survival due to significantly increased CD8+ T cell infiltration determined via immunohistochemistry (IHC) as well as flow cytometry.

Figure 4A:
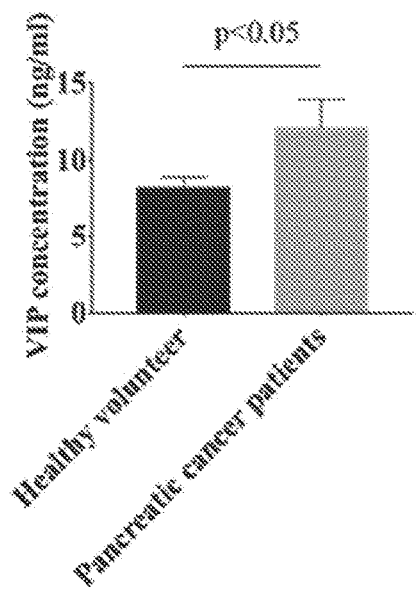
FIG. 4A shows data indicating elevated VIP levels in human pancreatic cancers. Serum isolated from peripheral blood of PDAC patients and healthy volunteers, was tested for VIP levels using VIP specific enzyme immunoassay, shows significantly elevated VIP levels in PDAC patients.
Figure 4B:
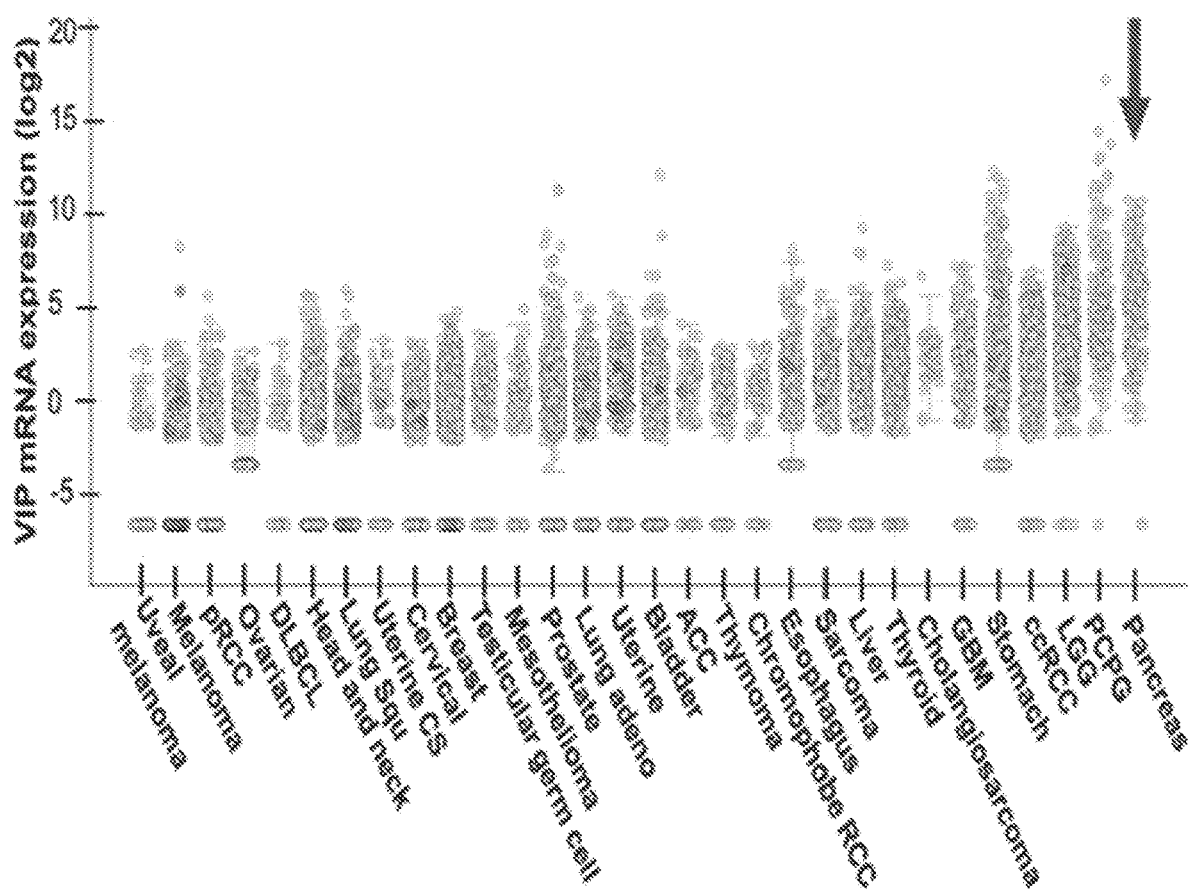
FIG. 4B shows data from the cancer genome atlas (TCGA) indicating elevated VIP mRNA expression in human exocrine pancreatic cancer (arrow).
Figure 4C:
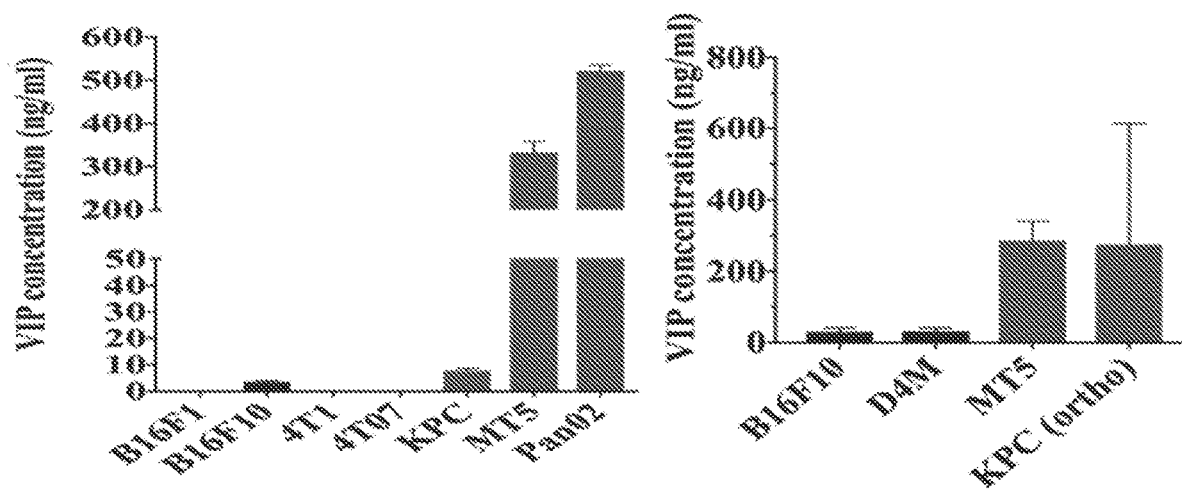
FIG. 4C shows data indicating elevated VIP levels in murine pancreatic cancers. Cell culture supernatant collected from melanoma, breast and pancreatic cancer cell lines, 24 hours after culture were tested for VIP levels (n=3) using VIP specific enzyme immunoassay (VIP.EIA).

Cell culture supernatants collected from pancreatic cancer cell lines have elevated levels of VIP when compared to that from melanoma and breast cancer cell lines (FIG. 4C). Mice bearing subcutaneously injected MT5 (pancreatic cancer cell line), B16F10 or D4M (melanoma cell lines) or orthotopically injected KPC (pancreatic cancer cell line) were terminally bled and sacrificed when the tumors were 500 mm$^3$. Serum isolated from the blood were tested for VIP levels using VIP.EIA. Mice bearing pancreatic cancers have elevated levels of VIP when compared to that in mice bearing melanoma tumors. Healthy skin tissue and tumor tissue sections from subcutaneous MT5 and orthotopic KPC bearing mice were stained for expression of VIP (not shown). Both tumor tissues confirmed the local expression of VIP.

VIPhyb and Anti-PD1 Therapy Improves Survival and Delayed Tumor Progression in Mouse Models of PDAC.

Figure 5:
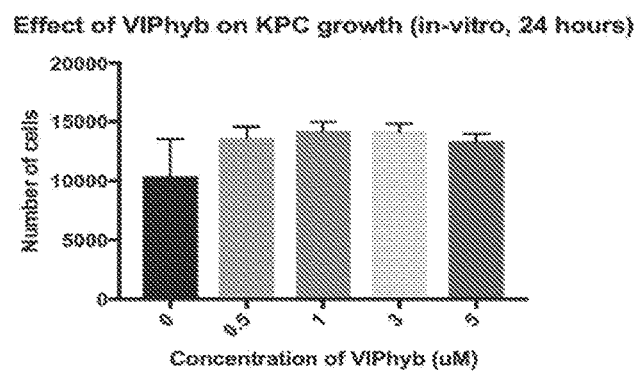
FIG. 5 shows data indicating VIPhyb does not directly kill the pancreatic cancer cells in-vitro.

KPC luc pancreatic cancer cells were cultured in a 96 well plate for 24 hours with different concentrations of VIPhyb (0, 0.5, 1, 3 and 5 uM). Number of viable cells after 24 hours were quantified via MTT assay. The data shows that VIPhyb does not directly kill the pancreatic cancer cells in-vitro (FIG. 5).

Level of secreted VIP in 1) serum of healthy volunteers, 2) untreated PDAC patients, 3) cell culture supernatant from murine melanoma, breast and PDAC cells and 4) serum from mice bearing these cell lines were tested. Effect of inhibiting VIP signaling in-vivo was tested using VIPhyb. Mice were subcutaneously inoculated with luciferase transfected KPC (KPC luc), PDAC cell lines, and treated with VIPhyb and/or anti-PD1 treatment after the tumors were palpable. The treatment regimen involved administering 10 μg VIPhyb subcutaneously, every day and 200 μg anti-PD1 or IgG2a, intraperitoneally, every three days, for 10 days. The tumors were measured using calipers or imaged via IVIS imaging system. The mice were sacrificed when tumors ulcerated or when they reached IACUC endpoint. Immunohistochemistry was performed on tumor tissue sections harvested at the time of sacrifice for expression of VIP, CD8 and DAPI.

Treatment of immune competent mice bearing KPC luc PDAC cells with the combination of VIPhyb and anti-PD1 produced complete and durable regression of tumors in 20% of the mice and delayed tumor progression in both tumor models. Further, upon analysis of the tumor tissues sections, significant infiltration of CD8+ T cells was observed in mice treated with the combination of VIPhyb and anti-PD1. Tumor tissue sections obtained from MT5 bearing mice treated with anti-PD1 or anti-PD1+VIPhyb were stained for expression of VIP and CD8. The mice treated with VIPhyb and anti-PD1 shows increased infiltration of CD8+ T cells into the tumor.

Figure 6B:
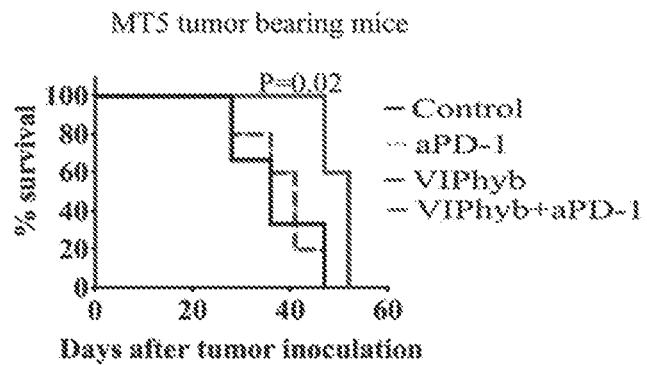
FIG. 6B shows data on MT5 cells.
Figure 7:
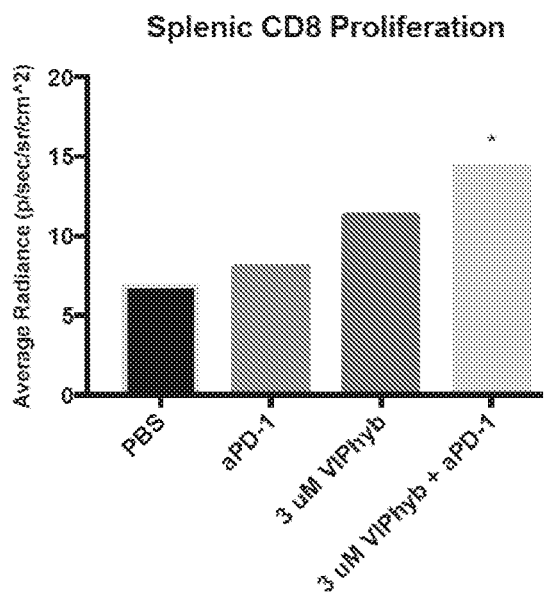
FIG. 7 shows data VIPhyb+anti PD-1 increases proliferation of CD8+ T cells responding to melanoma.

KPC luc pancreatic cancer cells were cultured in a 96 well plate for 24 hours with different concentrations of VIPhyb (0, 0.5, 1, 3 and 5 uM). Number of viable cells after 24 hours were quantified via MTT assay. The data shows that VIPhyb does not directly kill the pancreatic cancer cells in-vitro (FIG. 6).

The invention claimed is:

1. A method of enhancing the immune response to a cancer or treating a cancer in a subject in need thereof comprising administering an antagonist of vasoactive intestinal peptide signalling in combination with an antibody to immune check-point molecule to the subject, wherein the cancer is leukaemia, melanoma, pancreatic cancer, Hodgkin lymphoma, bladder cancer, kidney cancer, colon cancer, lung cancer, or breast cancer, and wherein the antibody to immune check-point molecule is an anti-PD-1 antibody or an anti-PD-L1 antibody.

2. The method of claim 1, wherein the subject is diagnosed with pancreatic cancer.

3. The method of claim 1, wherein the subject is diagnosed with melanoma.

4. The method of claim 1, wherein the anti-PD-1 antibody is pembrolizumab or nivolumab.

5. The method of claim 1, wherein the anti-PD-L1 antibody is atezolizumab, avelumab, or durvalumab.

6. The method of claim 1, wherein the antibody to immune check-point molecule is ipilimumab.

7. The method of claim 1 wherein the subject is a human.

8. The method of claim 1 in which the vasoactive intestinal polypeptide antagonist is composed of the sequence (SEQ ID NO: 1) KPRRPYTDNYTRLRKQMAVKKYLNSILN.

9. The method of claim 1, wherein the VIP antagonist is selected from the group consisting

[Ac-Tyr1,D-Phe2]GRF 1-29, amide, i.e., (SEQ ID NO: 4) YFDAIFTNSYRKVLGQLSARKLLQDIMSR (Modifications: Tyr-1=N-terminal Ac, Phe-2=D-Phe, Arg-29=C-terminal amide);

VIP (6-28), i.e., (SEQ ID NO:5) FTDNYTRLRKQMAVKKYLNSILN (Modifications: Asn-23=C-terminal amide);

[D-p-Cl-Phe6, Leu17]-VIP, i.e., (SEQ ID NO: 6) HSDAVFTDNYTRLRKQLAVKKYLNSILN (Modifications: Phe-6=p-Cl-D-Phe, Asn=C-terminal amide);

N-terminal Stearyl, Norleucine 17 VIPhyb, i.e., (SEQ ID NO: 9) KPRRPYTDNYTRLRKQXAVKKYLNSILN, wherein X is norleucine;

Ac His1 [D-Phe(2), Lys(15), Arg(16), Leu(27)]-VIP(1-7)/GRF(8-27), i.e., (SEQ ID NO:10) HFDAVFTN-SYRKVLKRLSARKLLQDIL, C-terminal amide; and pituitary adenylate cyclase-activating polypeptide, PACAP (6-38) C-terminal amide, i.e., (SEQ ID NO:11) TDSYSRYRKQMAVKKY-LAAVLGKRYKQRVKNK.

10. The method of claim 1, wherein the cancer is leukaemia.

11. The method of claim 1, wherein the cancer is Hodgkin lymphoma.

12. The method of claim 1, wherein the cancer is bladder cancer.

13. The method of claim 1, wherein the cancer is kidney cancer.

14. The method of claim 1, wherein the cancer is colon cancer.

15. The method of claim 1, wherein the cancer is breast cancer.

* * * * *

UNITED STATES PATENT AND TRADEMARK OFFICE
CERTIFICATE OF CORRECTION

| | | |
|---|---|---|
| PATENT NO. | : 11,471,506 B2 | Page 1 of 2 |
| APPLICATION NO. | : 17/050376 | |
| DATED | : October 18, 2022 | |
| INVENTOR(S) | : Edmund K. Waller et al. | |

It is certified that error appears in the above-identified patent and that said Letters Patent is hereby corrected as shown below:

On the Title Page

Replace the title page with the attached title page showing the corrected number of claims.

In the Claims

Column 29 Line 41 Delete Claim 6.

Renumber Claim 7 to Claim 6.

Renumber Claim 8 to Claim 7.

Renumber Claim 9 to Claim 8.

Renumber Claim 10 to Claim 9.

Renumber Claim 11 to Claim 10.

Renumber Claim 12 to Claim 11.

Renumber Claim 13 to Claim 12.

Renumber Claim 14 to Claim 13.

Renumber Claim 15 to Claim 14.

Signed and Sealed this
First Day of April, 2025

Coke Morgan Stewart
*Acting Director of the United States Patent and Trademark Office*

(12) United States Patent
Waller et al.

(10) Patent No.: US 11,471,506 B2
(45) Date of Patent: Oct. 18, 2022

(54) VIP ANTAGONISTS AND USES IN TREATING CANCER

(71) Applicants: Emory University, Atlanta, GA (US); Georgia Tech Research Corporation, Atlanta, GA (US)

(72) Inventors: Edmund K. Waller, Atlanta, GA (US); Rebecca Pankove, Atlanta, GA (US); Susan Thomas, Atlanta, GA (US); Sruthi Ravindranathan, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 17/050,376

(22) PCT Filed: Apr. 24, 2019

(86) PCT No.: PCT/US2019/028914
§ 371 (c)(1),
(2) Date: Oct. 23, 2020

(87) PCT Pub. No.: WO2019/209952
PCT Pub. Date: Oct. 31, 2019

(65) Prior Publication Data
US 2021/0046152 A1 Feb. 18, 2021

Related U.S. Application Data

(60) Provisional application No. 62/661,236, filed on Apr. 23, 2018.

(51) Int. Cl.
*A61K 38/00* (2006.01)
*A61K 38/16* (2006.01)
*A61P 35/00* (2006.01)
*C07K 16/28* (2006.01)

(52) U.S. Cl.
CPC .............. *A61K 38/16* (2013.01); *A61P 35/00* (2018.01); *C07K 16/2818* (2013.01); *C07K 16/2827* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 5,225,539 A | 7/1993 | Winter |
| 5,565,424 A | 10/1996 | Gozes et al. |
| 5,585,089 A | 12/1996 | Queen et al. |
| 5,693,761 A | 12/1997 | Queen et al. |
| 5,693,762 A | 12/1997 | Queen et al. |
| 5,859,205 A | 1/1999 | Adair et al. |
| 6,300,064 B1 | 10/2001 | Knappik et al. |
| 6,407,213 B1 | 6/2002 | Carter et al. |
| 6,828,304 B1 | 12/2004 | Burman et al. |
| 7,094,755 B2 | 8/2006 | Burman et al. |
| 7,125,689 B2 | 10/2006 | Carr et al. |
| 7,264,806 B2 | 9/2007 | Carr et al. |

OTHER PUBLICATIONS

National Institutes of Health, PDL1 (Immunotherapy) Tests, last visited, Oct. 28, 2021.*
Siedel et al. 2018, Anti-PD-1 and Anti-CTLA-4 Therapies in Cancer: Mechanisms of Action, Efficacy, and Limitations. Frontiers in oncology, 8: 86.*
Yao et al. (2018) Cancer Cell-Intrinsic PD-1 and Implications in Combinatorial Immunotherapy. Front. Immunol. 9:1774.*
Brentjens, Renier J., et al. "CD19-targeted T cells rapidly induce molecular remissions in adults with chemotherapy-refractory acute lymphoblastic leukemia." Science translational medicine 5.177 (2013): 177ra38-177ra38.
Filaci, Gilberto, et al. "CD8+ CD28− T regulatory lymphocytes inhibiting T cell proliferative and cytotoxic functions infiltrate human cancers." The Journal of Immunology 179.7 (2007): 4323-4334.
Hodi, F. Stephen, et al. "Improved survival with ipilimumab in patients with metastatic melanoma." New England Journal of Medicine 363.8 (2010): 711-723.
Montes, Carolina L., et al. "Tumor-induced senescent T cells with suppressor function: a potential form of tumor immune evasion." Cancer research 68.3 (2008): 870-879.
Pentcheva-Hoang, Tsvetelina, Emily Corse, and James P. Allison. "Negative regulators of T-cell activation: potential targets for therapeutic intervention in cancer, autoimmune disease, and persistent infections." Immunological reviews 229.1 (2009): 67-87.
Petersen, Christopher, Jian-Ming Li, and Edmund Waller. "Administration of a vasoactive intestinal peptide antagonist significantly enhances the autologous anti-leukemia T cell response in a murine model of AML." Journal for ImmunoTherapy of Cancer 3.2 (2015): 1-4., 3(Suppl 2):P238.
Porter, David L., et al. "A phase I trial of donor lymphocyte infusions expanded and activated ex vivo via CD3/CD28 costimulation." Blood 107.4 (2006): 1325-1331.
Ramello, María Cecilia, et al. "Tumor-induced senescent T cells promote the secretion of pro-inflammatory cytokines and angiogenic factors by human monocytes/macrophages through a mechanism that involves Tim-3 and CD40L." Cell death & disease 5.11 (2014): e1507-e1507.
Schudel et al. "S-Nitrosated Polypropylene Sulfi de Nanoparticles for Thiol-Dependent Transnitrosation and Toxicity Against Adult Female Filarial Worms" Adv. Healthcare Mater. 2015, 4, 1484-1490.

(Continued)

*Primary Examiner* — Jeanette M Lieb
(74) *Attorney, Agent, or Firm* — Meunier Carlin & Curfman LLC

(57) ABSTRACT

This disclosure relates to methods of treating cancer or viral infections comprising administering an effective amount of a VIP antagonist in combination with an immune check-point inhibitor to a subject in need thereof. In certain embodiments, the immune check-point inhibitor is an anti-PD1 or anti-PDL1 antibody.

14 Claims, 6 Drawing Sheets

Specification includes a Sequence Listing.